United States Patent [19]

Shimonaka et al.

[11] Patent Number: 4,809,679
[45] Date of Patent: Mar. 7, 1989

[54] FORCEPS PLUG FOR ENDOSCOPES

[75] Inventors: Kideki Shimonaka, Hachioji; Ichiro Nakamura, Musashino, both of Japan

[73] Assignee: Olympus Optical Co., Ltd., Japan

[21] Appl. No.: 107,946

[22] Filed: Oct. 13, 1987

[30] Foreign Application Priority Data

Nov. 19, 1986 [JP] Japan ................ 61-277672
May 26, 1987 [JP] Japan ............... 62-79393[U]

[51] Int. Cl.⁴ ............................................. A61B 1/00
[52] U.S. Cl. ............................... 128/4; 604/167
[58] Field of Search ................... 128/4, 3, 5, 6; 604/167, 197, 198, 202, 215, 236, 237, 238, 256, 415

[56] References Cited

U.S. PATENT DOCUMENTS 3,853,127 12/1974 Spademan ............. 604/167
4,146,019 3/1979 Bass et al. .............. 128/6
4,649,904 3/1987 Krauter et al. .......... 128/6
4,653,477 3/1987 Akui et al. .............. 128/4
4,715,360 12/1987 Akui et al. .............. 128/4

FOREIGN PATENT DOCUMENTS 61-57901 4/1986 Japan .
61-131723 6/1986 Japan .

Primary Examiner—William H. Grieb
Attorney, Agent, or Firm—Ostrolenk, Faber, Gerb & Soffen

[57] ABSTRACT

A forceps plug for endoscopes comprises energizing means for partly pressing only the center on an outer peripheral portion of an elastic plug body which portion corresponds to a slit provided in the latter and is in a direction substantially perpendicular to the slit, in a direction to close the slit and for extending the slit in it longitudinal direction.

7 Claims, 3 Drawing Sheets

FORCEPS PLUG FOR ENDOSCOPES

BACKGROUND OF THE INVENTION

The present invention relates to a forceps plug for endoscopes, and more particularly, to a forceps plug for endoscopes which is to be fitted into a forceps plug holding frame provided on an endoscope operation body to form an opening for inserting and withdrawing medical treatment instruments to retain a seal of the opening.

As is well known, a forceps plug holding frame which forms an opening for inserting instruments for medical treatment, biopsy and the like into a forceps channel is provided on an endoscope operation body to fit a forceps plug thereinto.

Specifically, as shown in FIG. 1, a forceps plug holding frame 4 is integrally provided on an operation body 3 of an endoscope 2 and a forceps plug 1 for endoscopes is fitted in the frame 4. An opening for medical treatment instruments is formed on the frame 4 and is in communication with a forceps channel formed by a tube for channels (not shown) disposed through the operation body 3 and a body cavity insertable portion 5.

As is well known, the forceps plug 1 hermetically seals the forceps channel against the exterior at an opening thereof during operations such as suction and opens the opening when a medical treatment instrument, an injection pipe for introducing fluids or the like is inserted. In addition, FIG. 1 shows an eyepiece 6, a suction pipe 7 and a suction apparatus 8.

In the past, the forceps plug 1 for endoscopes of the type described above, as shown in FIGS. 2 and 3, comprises an elastic member made of rubber or the like of an M-shaped configuration in a longitudinal section and having a slit 9 for insertion in a diametrical direction at the central bottom wall portion of a spherical recess 1a is provided in the upper central part thereof. The slit 9 is to be normally closed by placing both its side walls into close contact with each other under its resilience. The plug 1 is removably and resiliently fitted in the opening of the frame 4. When a forceps 10 for biopsy or the like is inserted into the opening of the frame 4, as shown in FIG. 2, a tip of the forceps 10 is introduced into the slit 9 against its resilience. At this time, since both side walls of the slit 9 are resiliently placed into close contact with each other, a seal against the exterior can be retained. In addition, in the conventional forceps plug described above, there have been proposed that a wall thickness of the slit portion is changed in order to further improve a seal (Japanese Laid-open Patent Application No. Sho 61/1986-131723) and the inner periphery of the plug holding frame is placed into close contact with or pressed to the whole outer periphery of the slit portion in an elastic plug body in order to prevent reduction of the close contact due to yielding of the elastic plug body (Japanese Laid-open Utility Model Application No. Sho 61/1986-57901).

As such, although various measures have been devised to assure a seal of a forceps plug, since medical treatment instruments, injection pipes and the like are frequently inserted in or withdrawn from channels of an endoscope by spreading the slit to perform medical treatment and supply of fluids and medicines, the close tightness of the slit may be reduced due to wear and yielding, thus deteriorating effectiveness as a seal. As a result, when a suction operation is effected, air is drawn in from the exterior to lower the suction capability at the tip of a channel, to leak filth sucked in from a patient body to the exterior through the slit and to pollute an operator by spurting out filth within a bronchial tube when a patient has a coughing fit with a bronchoscope. In addition, in order to prevent lowering sealing effectiveness due to wear and yielding in a slit portion of an elastic plug body, it is conceivable that a thickness of the slit portion is increased or an inner periphery of a plug holding frame is placed into closer contact with or more pressed to the whole outer periphery of the slit portion. With these measures, however, although sealing at the slit may be improved, the opening capability of the slit would be deteriorated. As a result, the insertability of medical treatment instruments and injection pipes also would be deteriorated to result in breakage of the instruments and difficulty in introducing fluids.

SUMMARY OF THE INVENTION

It is an object of the present invention to provide a forceps plug for endoscopes which improves a seal and prevents lowering operability as indicated above.

According to the present invention, energizing means for partially pressing only the center on an outer peripheral portion of an elastic plug body which portion corresponds to a slit provided in the latter and is in a direction substantially perpendicular to the slit, in a direction to close the slit and for extending the slit in its longitudinal direction are provided, so that ① as compared with a conventional forceps plug, a close tightness in the slit can be increased to much improve a seal and lowering the suction capability in a suction operation and pollution by spurting out filth in a patient body from the slit can be eliminated, ② even though wear and yielding may be caused in the slit by repeatedly inserting medical treatment instruments and injection pipes, the close tightness is maintained and the seal is not deteriorated, and ③ while retaining the seal, opening ability of the slit is not greatly lowered, hence retaining a good insertability of the instruments.

DETAILED DESCRIPTION OF PREFERRED EMBODIMENT

Figure 1:
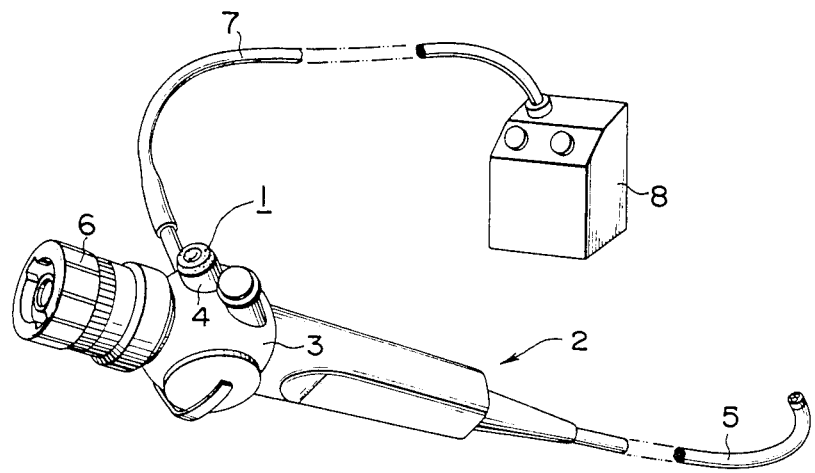
FIG. 1 is a perspective view illustrating an example of endoscopes for medical treatment.
Figure 2:
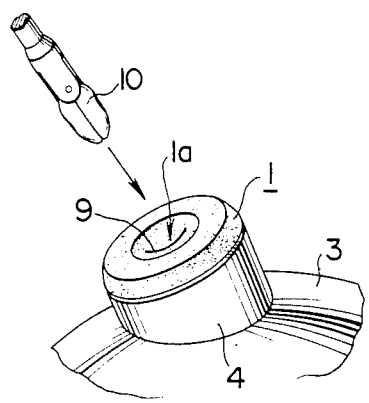
FIG. 2 is a perspective view illustrating introduction of a forceps into an opening for forceps fitted with a conventional forceps plug.
Figure 3:
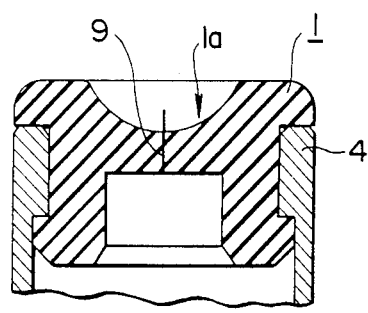
FIG. 3 is a longitudinal section view illustrating an example of a conventional forceps plug.
Figure 4:
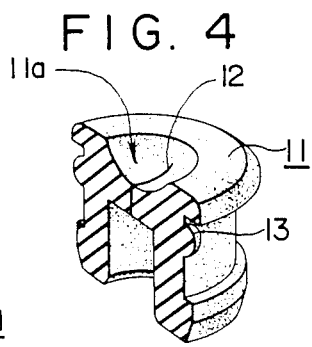
FIG. 4 is a perspective view illustrating a longitudinal right half section of a forceps plug according to a first embodiment of the present invention.
Figure 5:
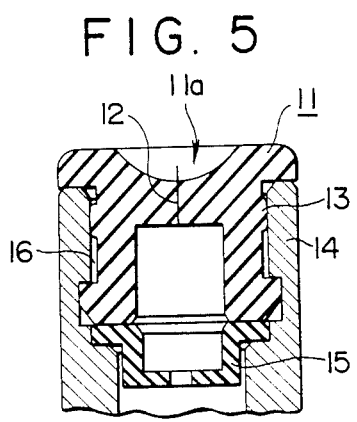
FIG. 5 is a longitudinal section view illustrating the forceps plug shown in FIG. 4 fitted in a forceps plug holding frame.
Figure 6:
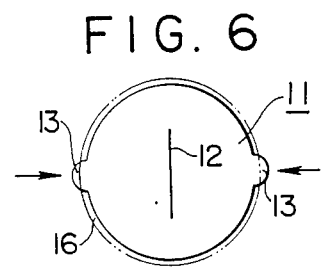
FIG. 6 is a diagram illustrating actions of the forceps plug and forceps plug holding frame shown in FIG. 5.

In FIG. 4 and 5, which illustrates a first embodiment of the present invention, a forceps plug 11 comprises an elastic member of an M-shaped configuration in section which is made of rubber, soft synthetic resin or the like and has a slit 12 in a diametric direction in the central bottom wall portion of the spherical recess 11a provided on the upper central portion thereof. Diametrically opposed hemispherical projections 13 are provided on the side periphery of the plug 11, that is, on the outer peripheral portion corresponding to a portion provided with the slit 12, in a position substantially perpendicular to the slit 12, at a smaller part than a length of the slit 12 (FIG. 6). In FIG. 5, numeral 14 represents a forceps plug holding frame provided on an endoscope operation body which has an opening for insertion and withdrawal of a forceps and numeral 15 represents an inner valve fitted in the frame 14 together with the forceps plug 11 and numeral 16 represents a cavity formed between an outer periphery on which the projection 13 is formed and an inner periphery of the forceps plug holding frame 14 into which the forceps plug 11 is fitted.

When the forceps plug 11 is detachably fitted into the forceps plug holding frame 14 made of metal, hard synthetic resin or the like under resilience of the forceps plug 11 as shown in FIG. 5, the forceps plug 11 is urgingly pressed at the central portion of the slit 12 by action between the projection 13 and the inner periphery of the frame 14 only in a direction perpendicular to the slit 12 as shown in FIG. 6. Consequently, a close tightness in the slit 12 is increased and even when wear and yielding are caused by repeatedly inserting medical treatment instruments and injection pipes a seal can be retained, so that there is no possibility of lowering of a suction force and leakage or spurt of filth during suction. In addition, since the slit 12 is pressed only at its small central part and other parts than those in a direction perpendicular to the slit 12 are deformable as noted from FIG. 6, there is no possibility of greatly disturbing insertion of medical treatments and injection pipes.

Figure 7:
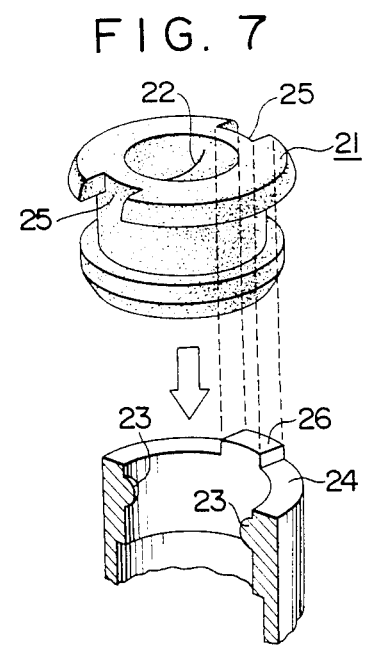
FIG. 7 is an exploded perspective view of a forceps plug and a forceps plug holding frame according to a second embodiment of the present invention.
Figure 8:
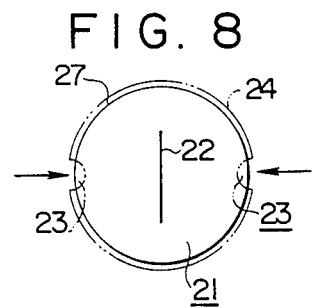
FIG. 8 is a diagram illustrating actions of the forceps plug and the forceps plug holding frame shown in FIG. 7.

In FIG. 7, which shows a second embodiment of the present invention, a forceps plug 21 has no projection corresponding to the projection 13 of the forceps plug 11 shown in FIG. 4 and instead a pair of notched portions 25 for positioning are provided on peripheral side of an upper flange in a direction of a slit 22. A pair of projections 26 for positioning which fit into the notched portions 25 of the forceps plug 21 are provided on the front end surface of a forceps plug holding frame 24 into which the forceps plug 21 is fitted. A pair of hemispherical projections 23 are provided towards upper of the inner periphery of the forceps plug holding frame in opposed relationship with each other in a direction perpendicular to the line connecting the pair of projections 26 (FIG. 8). Numeral 27 represents a cavity corresponding to the cavity 16 shown in FIG. 6.

In the second embodiment, when the forceps plug 21 is fitted in the holding frame 24, as shown in FIG. 8, the projections 23 energize to press the outer periphery of the forceps plug 21. While this is contrary to the case between the forceps plug 21 and its holding frame 14 shown in FIG. 4, the fact that the slit 22 of the forceps plug 21 is pressed only at the central portion of the slit 22 in a direction perpendicular to the slit 22 and thus its action and effects are the same as in the first embodiment.

Figure 9:
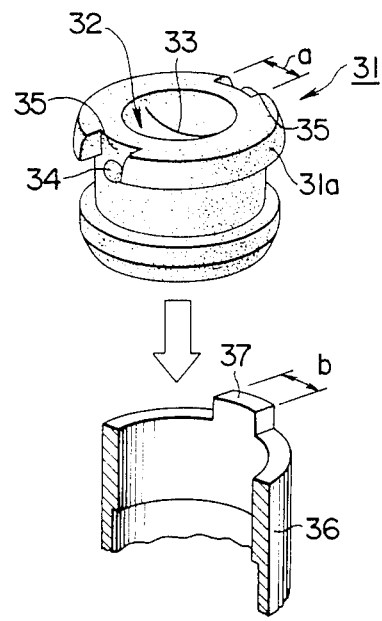
FIG. 9 is an exploded perspective view of a forceps plug and a forceps plug holding frame of a third embodiment according to the present invention.
Figure 10:
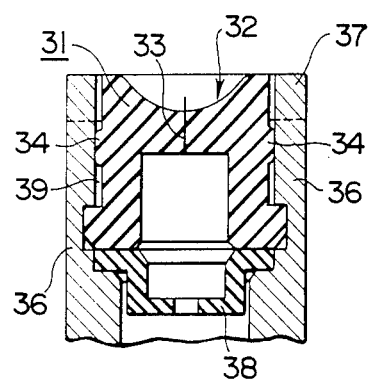
FIG. 10 is a longitudinal section view of the forceps plug fitted in forceps plug holding plug shown in FIG. 9.

In FIGS. 9 and 10, which shows a third embodiment of the present invention, a forceps plug 21 comprises an elastic member of an M-shaped configration insection which is made of rubber, soft synthetic resin or the lite. A slit 33 in a diametrical direction is provided in the central bottom wall portion of a spherical recess 32 provided on the upper central portion of the plug 31. A pair of oppositely extending diametrically opposed hemispherical projection 34 are provided at a position towards upper of the peripheral side of the plug 31, that is, a position at substantially the same level as the slit 33 and at a position in a direction substantially perpendicular to the slit 33. The diameter of each projection 34 is much less than the length of the slit 33. A pair of notched portions 35 are provided on an upper flange 31a of the plug 31 at positions above the projections 34 in opposed relationship with each other. On the other hand, a pair of projections 37 (only one is shown in FIG. 9) are provided on the upper plane of a forceps plug holding frame 36 of a cylindrical form made of metal, hard synthetic resin or the like into which the forceps plug 31 is fitted, in facing relationship with the notched portions 35 so as to fit thereinto. A length b of the projection 37 is slightly longer than a length a of the notched portion 35 so that the projection 37 is in press fit to secure the forceps plug 31 to the holding frame 36. In FIG. 10, numeral 38 represents an inner valve to be fitted into the frame 36 together with the forceps plug 31 below the latter, numeral 39 represents a cavity formed between the outer periphery of the forceps plug 31 and the inner periphery of the holding frame 36.

When the forceps plug 31 is detachably mounted on the holding frame 36 as shown in FIG. 10, both projections 34 of the forceps plug 31 are pressed against the right and left inner sides of the projections 37 of the frame 36, so that the central portion of the slit 33 is urgingly pressed only in a direction perpendicular to the slit 33. In addition, since a width b of the projection 37 is slightly longther than a width a of the notched portion 35 of the plug 31, both sides of the slit 33 are energized so as to be extended in its direction. Consequently, the close tightness in the slit 33 is increased, so that it is possible to retain the seal of the slit 33 even when wear and yielding are caused by repeatedly inserting medical treatment instruments and injection pipes. On the other hand, since the slit 33 is energized in its direction by engagement of the notched portion 35 is energized in its direction by engagement of the notched portion 35 with the projection 37, it is possible to prevent occurrence of both side filmy portions of the slit being superimposed when medical treatment instruments and injection pipes are obliquely pulled out. In addition, there is no possibility of lowering of a suction force and leakage or spurting out filth during suction. The slit 33 is urgingly pressed only at its small central portion and are deformable in other directions than the perpendicular to slit 33, so that there is no possibility of greatly disturbing insertion of medical treatment instruments and injection pipes.

Figure 11:
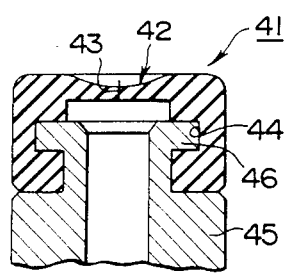
FIG. 11 is a longitudinal section view of a forceps plug fitted in a forceps plug holding frame illustrating a fourth embodiment of the present invention.
Figure 12:
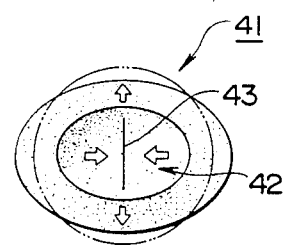
FIG. 12 is a plan view of the forceps plug shown in FIG. 11.

In FIGS. 11 and 12, which shows a fourth embodiment of the present invention, a forceps plug 41 comprises an elastic member of an M-shaped configuration insection which is made of rubber, soft synthetic resin or the like. The plug 41, as shown in FIG. 12, is in an elliptical form in a plan view and a recess 42 of the plug 41 also is in an elliptical form in which a slit 43 is provided in a direction of its short axis. In addition, a fitting groove 44 is provided on the inner periphery of the plug 41 for mounting the plug 41 on an upper end flange 46 of a forceps plug holding frame 45 made of hard material. The groove 44 is also in an elliptical form like the external form of the plug 41.

The forceps plug holding frame 45 on which the plug 41 is mounted is in a cylindrical form and the flange 46 also is in a cylindrical form. Consequently, when the forceps plug 41 is fitted onto the forceps plug holding frame 45, the forceps plug 41 made of a resilient material deforms against the resilience as shown with a broken line in FIG. 12 into a cylindrical form. The forceps plug 41 deformed in a cylindrical form exerts actions on the slit 43 with its restoring ressilient force to produce a force urgingly pressing the slit in a direction to close it and simultaneously a force extending in a direction of the slit, so that it is possible to obtain the same actions and effects as in the forceps plug 31 shown in FIG. 9.

What is claimed is:

1. A forceps plug for endoscopes comprising an elastic plug body provided with a slit therein for inserting and withdrawing medical treatment instruments, fluid feeding pipes and the like, said plug body being fitted into a forceps plug holding frame provided on an endoscope operation body for forming an opening for insertion and withdrawal of the instruments so as to retain a seal of the opening, characterized in that energizing means for urgingly pressing said slit only at a slit portion located in a direction substantially perpendicular thereto in a direction to close said slit is provided on an outer peripheral portion of said plug body corresponding to said slit.

2. A forceps plug for endoscopes according to claim 1 in which said energizing means comprises a projection of a smaller width than the length of said slit provided at a position in a direction substantially perpendicular to the slit on the outer periphery of said elastic plug body and an inner surface of said forceps plug holding frame for pressing said projection.

3. A forceps plug for endoscopes according to claim 1 in which said energizing means comprises a projection provided on the inner surface of said forceps plug holding frame at a position in a direction substantially perpendicular to said slit of said elastic plug body and the outer periphery of the elastic plug body which is pressed by said projection.

4. A forceps plug for endoscopes according to claim 1 in which said energizing means is provided with a cavity formed between the outer periphery corresponding to the slit of said elastic plug body and the inner surface of said holding frame into which said elastic plug body is fitted, with the exception of a portion being pressed in the elastic plug body, for allowing deformation outwardly of the elastic plug body.

5. A forceps plug for endoscopes according to claim 1 in which the energizing means also presses said elastic plug body in a direction to extend said slit in its longitudinal direction.

6. A forceps plug for endoscopes according to claim 5 in which said energizing means for extending said slit comprises a pair of notched portions provided at symmetrical positions on a flange formed on the upper outer peripheral edge of said plug body in a direction of said slit and projections formed on the upper end surface of said plug holding frame of a cylindrical form, said projection having a width slightly larger than that of said notched portion so as to be pressed into the latter.

7. A forceps plug for endoscopes according to claim 5 in which said energizing means for extending said slit comprises an elastic plug body in a short tube body which is in an elliptical form in a plan view and which is provided with a fitting opening on the lower surface thereof, said plug body having a slit in a direction of the short axis in an elliptic recess of the upper central portion thereof, and a forceps plug holding frame of a cylindrical body having a slightly larger diameter than that of said plug body in its short axis direction so as to press said plug body against the outer periphery of the holding frame by allowing said plug body to deform.

* * * * *

UNITED STATES PATENT AND TRADEMARK OFFICE
CERTIFICATE OF CORRECTION

PATENT NO. : 4,809,679

DATED : MARCH 7, 1989

INVENTOR(S) : HIDEKI SHIMONAKA, ICHIRO NAKAMURA

It is certified that error appears in the above-identified patent and that said Letters Patent is hereby corrected as shown below:

ON THE TITLE PAGE:

Item [75]  -- CHANGE "KIDEKI" TO --HIDEKI--

Signed and Sealed this

Eighteenth Day of July, 1989

Attest:

DONALD J. QUIGG

Attesting Officer

Commissioner of Patents and Trademarks